United States Patent
Hammons et al.

(10) Patent No.: US 10,716,717 B2
(45) Date of Patent: *Jul. 21, 2020

(54) SANITARY NAPKIN FOR CLEAN BODY BENEFIT

(71) Applicant: The Procter & Gamble Company, Cincinnati, OH (US)

(72) Inventors: John Lee Hammons, Hamilton, OH (US); Susan Nicole Lloyd, Erlanger, KY (US); Stewart Lawrence Taub, Needham, MA (US)

(73) Assignee: The Procter & Gamble Company, Cincinnati, OH (US)

( * ) Notice: Subject to any disclaimer, the term of this patent is extended or adjusted under 35 U.S.C. 154(b) by 266 days.

This patent is subject to a terminal disclaimer.

(21) Appl. No.: 15/837,017

(22) Filed: Dec. 11, 2017

(65) Prior Publication Data

US 2018/0098894 A1 Apr. 12, 2018

Related U.S. Application Data

(63) Continuation of application No. 15/696,482, filed on Sep. 6, 2017, which is a continuation of application (Continued)

(51) Int. Cl.
*A61F 13/15* (2006.01)
*A61F 13/512* (2006.01)
(Continued)

(52) U.S. Cl.
CPC ........ *A61F 13/512* (2013.01); *A61F 13/5116* (2013.01); *A61F 13/51108* (2013.01); *A61F 13/511* (2013.01); *A61F 13/513* (2013.01); *A61F 13/51104* (2013.01); *A61F 2013/51182* (2013.01); *A61F 2013/51338* (2013.01); *A61F 2013/51344* (2013.01)

(58) Field of Classification Search
CPC ............. A61F 13/512; A61F 13/51108; A61F 13/511; A61F 13/51104; A61F 13/513; A61F 2013/51182; A61F 2013/51338; A61F 2013/51344
USPC .................. 604/378, 379, 380, 381, 385.101
See application file for complete search history.

(56) References Cited

U.S. PATENT DOCUMENTS 2,020,928 A 10/1934 Asnes
2,068,456 A 1/1937 Hooper
(Continued)

FOREIGN PATENT DOCUMENTS

EP 0 781 537 A1 7/1997
EP 1 022 007 A2 7/2000
GB 2 262 235 A 6/1993

OTHER PUBLICATIONS

PCT International Search Report dated Jun. 2, 2004, 7 pages.
(Continued)

*Primary Examiner* — Jacqueline F Stephens
(74) *Attorney, Agent, or Firm* — George H. Leal

(57) ABSTRACT

A disposable absorbent article having a facing layer joined to a backsheet and an absorbent core disposed between the facing layer and the backsheet, is described herein. The facing layer is a composite material having a plurality of apertures extending through the facing layer.

15 Claims, 3 Drawing Sheets

Related U.S. Application Data

No. 14/217,679, filed on Mar. 18, 2014, now Pat. No. 9,844,476, which is a continuation of application No. 13/219,085, filed on Aug. 26, 2011, now Pat. No. 8,704,036, which is a continuation of application No. 10/720,557, filed on Nov. 24, 2003, now Pat. No. 8,030,535.

(60) Provisional application No. 60/434,792, filed on Dec. 18, 2002.

(51) Int. Cl.
*A61F 13/511* (2006.01)
*A61F 13/513* (2006.01)

(56) References Cited

U.S. PATENT DOCUMENTS

| | | | |
|---|---|---|---|
| 2,177,490 A | 10/1939 | Kieffer | |
| 2,257,428 A | 9/1941 | Ruegenberg | |
| 2,275,425 A | 3/1942 | Grabec | |
| 2,404,758 A | 7/1946 | Teague | |
| 2,679,887 A | 6/1954 | Doyle | |
| 2,896,692 A | 7/1959 | Villoresi | |
| 2,901,951 A | 9/1959 | Hochfeld | |
| 3,081,500 A | 3/1963 | Griswold | |
| 3,081,512 A | 3/1963 | Griswold | |
| 3,236,718 A | 2/1966 | Cohn | |
| 3,351,441 A | 11/1967 | Gewiss | |
| 3,528,145 A | 9/1970 | Troope | |
| 3,542,634 A | 11/1970 | Such | |
| 3,681,182 A | 8/1972 | Kalwaites | |
| 3,681,183 A | 8/1972 | Kalwaites | |
| 3,881,987 A | 5/1975 | Renz | |
| 3,949,127 A | 4/1976 | Ostermeier | |
| 3,975,455 A | 8/1976 | Falender | |
| 4,100,324 A | 7/1978 | Anderson et al. | |
| 4,101,625 A | 7/1978 | Haley | |
| 4,116,392 A | 9/1978 | Schwarz | |
| 4,135,021 A | 1/1979 | Patchell | |
| 4,153,664 A | 5/1979 | Sabee | |
| 4,223,059 A | 9/1980 | Schwarz | |
| 4,223,063 A | 9/1980 | Sabee | |
| 4,276,336 A | 6/1981 | Sabee | |
| 4,285,100 A | 8/1981 | Schwarz | |
| 4,588,630 A | 5/1986 | Shimalla | |
| 4,588,879 A | 5/1986 | Noda et al. | |
| 4,758,297 A | 7/1988 | Calligarich | |
| 4,834,741 A | 5/1989 | Sabee | |
| 4,840,829 A | 6/1989 | Suzuki | |
| 4,968,313 A | 11/1990 | Sabee | |
| 5,143,679 A | 9/1992 | Weber | |
| 5,171,238 A * | 12/1992 | Kajander | A61F 13/512 604/366 |
| 5,254,111 A | 10/1993 | Cancio | |
| 5,300,055 A | 4/1994 | Buell | |
| 5,518,801 A | 5/1996 | Chappell et al. | |
| 5,626,571 A | 5/1997 | Young | |
| 5,628,097 A | 5/1997 | Benson | |
| 5,658,639 A | 8/1997 | Curro | |
| 5,691,035 A | 11/1997 | Chappell et al. | |
| 5,714,107 A | 2/1998 | Levy | |
| 5,723,087 A | 3/1998 | Chappell et al. | |
| 5,795,344 A | 8/1998 | Chappell | |
| 5,804,021 A | 9/1998 | Abuto | |
| 5,891,544 A | 4/1999 | Chappell et al. | |
| 5,895,380 A | 4/1999 | Turi et al. | |
| 5,895,623 A | 4/1999 | Trokhan | |
| 5,914,084 A | 6/1999 | Benson | |
| 5,916,661 A | 6/1999 | Benson | |
| 5,916,663 A | 6/1999 | Chappell et al. | |
| 5,964,742 A | 10/1999 | McCormack | |
| 5,968,029 A | 10/1999 | Chappell et al. | |
| 6,027,483 A | 2/2000 | Chappell et al. | |
| 6,049,024 A * | 4/2000 | Thomas | A61F 13/4755 604/367 |
| 6,059,764 A | 5/2000 | Osborn et al. | |
| 6,090,089 A | 7/2000 | Tsuji et al. | |
| 6,103,953 A | 8/2000 | Cree et al. | |
| 6,165,306 A | 12/2000 | Rajala | |
| 6,171,682 B1 | 1/2001 | Raidel et al. | |
| 6,264,872 B1 | 7/2001 | Majors | |
| 6,368,444 B1 | 4/2002 | Jameson | |
| 6,443,931 B1 | 9/2002 | Kurata | |
| 6,548,147 B1 | 4/2003 | Raidel et al. | |
| 6,911,574 B1 * | 6/2005 | Mizutani | A61F 13/512 604/380 |
| 8,030,535 B2 | 10/2011 | Hammons et al. | |
| 8,704,036 B2 | 4/2014 | Hammons et al. | |
| 2001/0029141 A1 | 10/2001 | Mizutani et al. | |
| 2002/0010449 A1 | 1/2002 | Mitzutani | |
| 2002/0019614 A1 | 2/2002 | Woon et al. | |
| 2003/0135182 A1 | 7/2003 | Woon et al. | |
| 2003/0224146 A1 | 12/2003 | Raidel et al. | |

OTHER PUBLICATIONS

EPO Search Report dated May 6, 2011, 6 pages.
All Office Actions for 13/219,085, filed Aug. 26, 2011.
All Office Actions for 14/217,679, filed Mar. 18, 2014.
All Office Actions for 10/720,557, filed Nov. 24, 2003.
All Office Actions for 15/696,482, filed Sep. 6, 2017.
All Office Actions for 15/584,165, filed May 16, 2017.
All Office Actions for 11/130,877, filed May 17, 2005.
All Office Actions for 10/217,911, filed Aug. 13, 2002.
All Office Actions for 09/544,886, filed Apr. 7, 2000.

* cited by examiner

SANITARY NAPKIN FOR CLEAN BODY BENEFIT

FIELD OF INVENTION

This invention relates to catamenial products such as sanitary napkins. In particular, this invention relates to body-facing layers for sanitary napkins that improve fluid acquisition and result in the wearer having a clean body.

BACKGROUND OF THE INVENTION

Body-facing layers of disposable absorbent products such as sanitary napkins, disposable diaper, and adult incontinence products are well known in the art. Body-facing layers are sometimes referred to as facing layers, and more commonly are referred to as topsheets.

Topsheets on disposable absorbent articles are fluid pervious sheets or webs; commonly nonwoven webs are utilized. Nonwoven webs provide fluid permeability along with softness. Although a nonwoven web can be used "as is" in many cases, it is often important to modify the nonwoven web for a particular purpose. For example, nonwoven webs for topsheets can be apertured, corrugated, or treated with fluid flow-modifying agents such as surfactants.

U.S. Pat. Nos. 5,916,661 and 5,628,097, both issued to Curro et al., disclose an apertured nonwoven web, and a method for making the web. This web has been found to be useful as a topsheet on disposable diapers, for example, by permitting viscous body exudates a pathway to an absorbent core within the diaper.

U.S. Pat. No. 5,518,801 issued to Chappell et al. discloses a process for forming a web, including laminates of webs, the process forming rib-like elements in a web. Such a process is disclosed as producing elastic-like webs from films, and the like. The elastic-like webs are formed by passing a web through the nip of a pair of intermeshing rolls that form the rib-like elements.

Both apertured and elastic-like webs made according to the processes disclosed in the above-mentioned Curro et al. and Chappell et al. patents have been disclosed separately for use in topsheets for disposable absorbent articles. However, there remains a need for topsheets effective in keeping the body of the wearer clean during use.

Accordingly, there is a need for a topsheet that is effective at absorbing body exudates, and at cleaning the skin of the wearer of any body exudates that remain on the skin during use.

SUMMARY OF THE INVENTION

A disposable absorbent article having a longitudinal axis defining a longitudinal orientation and longitudinally-oriented side edges, a transverse axis orthogonal to the longitudinal axis, a thickness measured orthogonal to a plane defined by the longitudinal axis and the transverse axis, and longitudinal side edges, the disposable absorbent article comprising: a facing layer, a backsheet, and an absorbent core disposed between the facing layer and the backsheet, wherein the facing layer comprises a composite material comprising a plurality of apertures extending through the facing layer.

A method of creating a composite material for use in a disposable absorbent article, the method comprising the steps of: obtaining a composite material; and simultaneously creating a first plurality of discontinuities and a second plurality of discontinuities in the composite material, wherein the first plurality of discontinuities and the second plurality of discontinuities are different.

DETAILED DESCRIPTION OF THE INVENTION

Figure 1:
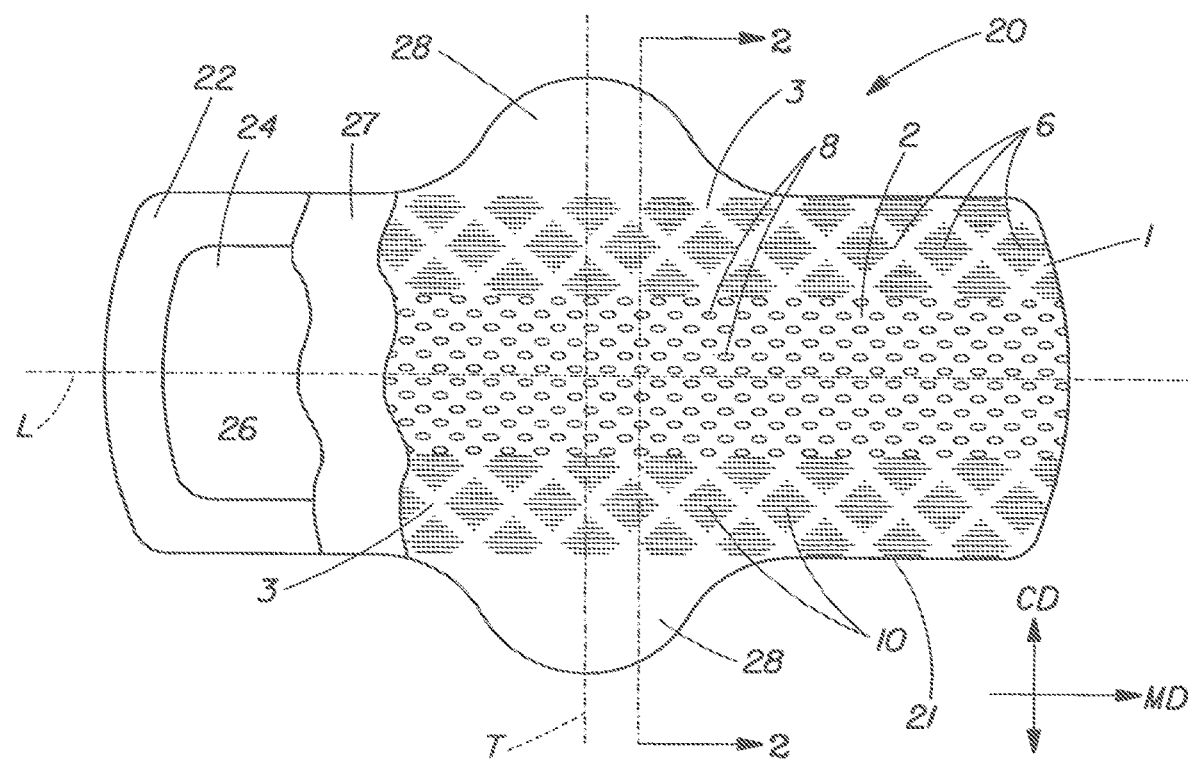
FIG. 1 is a plan view of a sanitary napkin of the present invention.

FIG. 1 shows in partial cut away plan view one embodiment of a sanitary napkin 20 of the present invention comprising a backsheet 22, a facing layer 1, and an absorbent core 24 disposed between the facing layer 1 and backsheet 22 which can be joined about a their periphery 21. Facing layer 1 can comprise a topsheet 26 alone, or together with a secondary topsheet 27 adjacent to and in contact with topsheet 26. Sanitary napkin 20 can have side extensions, commonly referred to as "wings" 28, designed to wrap the sides of the crotch region of the panties of the user of sanitary napkin 20. Wings 28 typically have fastening means (not shown) to releasably affix the sanitary napkin 20 to the panty.

Facing layer 1 of sanitary napkin 20 is a body-facing layer having a first region 2 and a second region 3, the two regions being differentiated by the kind of deformations 6 disposed in each. Facing layer 1 may comprise a topsheet 26 as is commonly known in the art, and it can be a composite comprising both topsheet 26 and secondary topsheet 27, also as known in the art. Sanitary napkins, including topsheets and secondary topsheets for use as the body facing surface thereof, are well known in the art and need no detailed description of various alternative and optional components and designs, all of which can form a part of the present invention.

Deformations 6 comprise apertures 8 and out-of-plane deformations 10 can be rib-like elements 10, each of which are important to providing the benefit of facing layer 1. In particular, apertures 8 are disposed in, and extend through, first region(s) 2 of the facing layer 1 and are sufficiently large (e.g., at least about 1 to 2 mm$^2$ each) to permit more viscous fluids, such as menses, to flow through the facing layer 1 and into absorbent core 24. First region 2, therefore, is preferably disposed generally centrally to sanitary pad 20, preferably along a centrally-disposed longitudinal axis L and at or near the junction of the L axis and a centrally disposed transverse axis T. Longitudinal axis L and transverse axis T define a two-dimensional plane of the sanitary napkin, which, in the embodiment shown is associated with the machine direction (MD) and cross machine direction (CD) as is commonly known in the art of making sanitary napkins in continuous processes.

Figure 2:
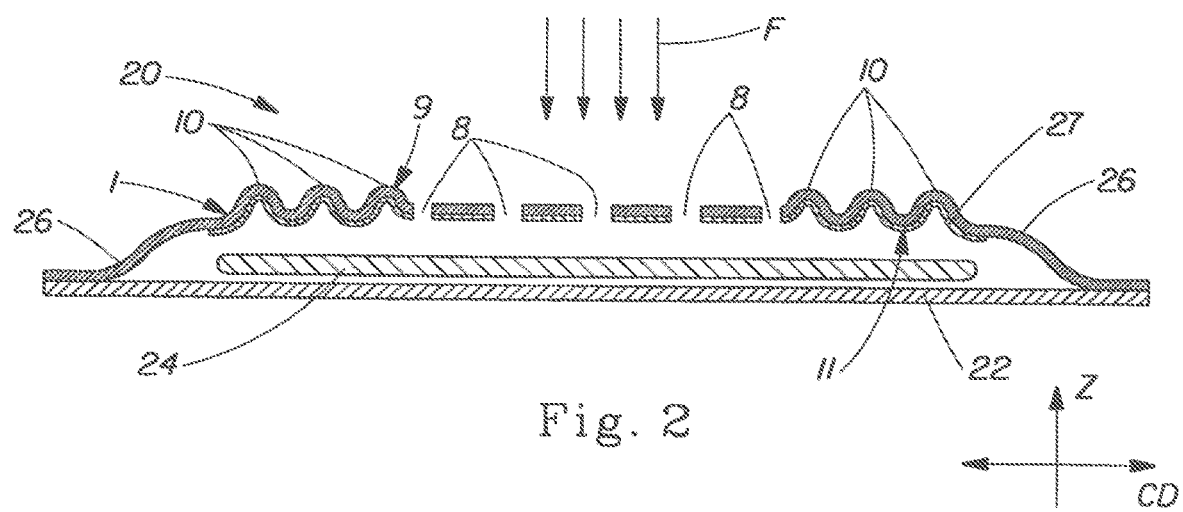
FIG. 2 is cross sectional view of Section 2-2 of FIG. 1.

Out-of-plane deformations 10 are disposed in second region 3 of facing layer 1. In general, by "out-of-plane" is meant extending in the "Z"-direction, as indicated by FIG. 2. In FIG. 2 out-of-plane deformations 10 are shown in exaggerated proportion, although there are not believed to be particular dimensional limitations. The only design considerations with respect to the dimensions of out-of-plane deformations 10 are those related to the comfort to the wearer. It may be that for particular facing layers 1 the height (Z-direction) of out-of-plane deformations 10 can be uniform; in other embodiments the height can vary, such as by increasing with increasing outboard distance from longitudinal centerline L. In one embodiment, out-of-plane deformations 10 are disposed generally outboard of first region 2, as shown in FIG. 1.

Out-of-plane deformations 10 can be rib-like elements, as shown in FIGS. 1 and 2. As such, out-of-plane deformations 10 can comprise raised ridges of a pre-defined length that is much shorter than the length of the sanitary napkin, measured along the longitudinal centerline, for example. In one embodiment as shown in FIG. 1, out-of-plane deformations 10 are disposed in a regular pattern of rib-like elements that form a pattern of diamond-shapes, each diamond shape being comprised of a plurality of rib-like elements. In this manner, the out-of-plane deformations 10 also contribute to softness and flexibility, as well as providing for improved visual perception of comfort. In general, the individual rib-like elements can have a length, measured along their longitudinal orientation, of between 1% and 50% of the length of the sanitary napkin, measured along the longitudinal axis. In a preferred embodiment, the individual rib-like elements can have a length of between 10% and 20% of the length of the sanitary napkin, with a spacing in the L-T plane such that there is not a straight path from any portion of the first region 2 to either of the longitudinal side edges of sanitary napkin 20.

In a preferred embodiment, first region 2 is disposed generally centrally with respect to the sanitary napkin. As shown in FIGS. 1-6, first region 2 can be disposed centrally and generally symmetrically with respect to the longitudinal axis L and transverse axis T. Second region 3 is preferably disposed outboard of first region 2 preferably in an area extending from first region 2 to an area adjacent longitudinal side edges of the sanitary napkin 20.

In general, the facing layer 1 can comprise nonwoven materials as are known in the art for topsheets on disposable absorbent articles. Absorbent core 24 and backsheet 22 can likewise comprise absorbent materials, and film materials, respectively, as is well known in the art. Secondary topsheet 27 (if used) can be a distribution layer that serves to distribute fluid in the directions of MD and CD. Wings, if used, can be integral extensions of the topsheet or the backsheet or both, and they can be symmetric about the longitudinal axis L, transverse axis T, or both.

The clean body benefit of the present invention is in part due to apertures 8 and out-of-plane deformations 10 that form discrete regions of facing layer 1. Apertures 8 provide for relatively unimpeded fluid flow of viscous fluid having a percentage of solids content, such as menstrual fluid. Raised, out-of-plane deformations 10 are a plurality of individual fluid barriers, each effective in retarding any free fluid flow that may have a tendency to run off the facing layer 1 when sanitary napkin 20 is used, without becoming a total block of fluid distribution to outboard portions of the sanitary napkin 20. In addition out-of-plane deformations 10 are soft, resilient, textured wipers to help keep the skin surfaces of the wearer clean.

As shown in FIG. 2, apertures 8 permit fluid communication between a body-contacting surface 9 of facing layer 1, and a second surface 11 of facing layer 1. Typically, second surface 11 is in contact with absorbent core 24 to effect efficient fluid flow into the core 24. Fluid typically flows from the body source in the direction of arrows F when the sanitary napkin is in use. However, it can be appreciated that menstrual fluid does not necessarily flow straight down in a gush, but, rather it flows out in contact with the wearer's skin onto the surface of the sanitary napkin. For this reason, it is important that fluid that otherwise has a tendency to follow the skin rather than enter the pad, be urged into the pad. It is believed that the raised, out-of-plane deformations 10 serves as a plurality of discrete wipers to urge, i.e., to wipe, fluid off the body and into the pad during use.

Additionally, since menses can have a substantial solids content, and can be relatively non-Newtonian, i.e., having a high viscosity relative to other fluids such as urine, the apertures 8 and out-of-plane deformations 10 aid in effective menses absorption into an absorbent core. Out-of-plane deformations 10 can act as barriers to prevent menses from migrating along the wearer's skin, and apertures 8 permit penetration of solids through facing layer 1.

It can also be appreciated with reference to FIG. 2 that fluid having a tendency to run off the facing layer 1 in the CD direction will be impeded by raised, out-of-plane deformations 10 generally disposed along the longitudinal side edges of sanitary napkin 20. Although all the raised, out-of-plane deformations 10 are shown as being aligned longitudinally in the MD, this is just a currently preferred embodiment. In practice, raised, out-of-plane deformations 10 could be oriented otherwise.

In the preferred embodiments shown, apertures 8 and raised, out-of-plane deformations 10 are shown in a longitudinally-aligned orientations. This is due to the preferred method for making, as disclosed below. But it is recognized that other patterns of apertures and deformations are within the scope of the invention, including, for example, a discrete region in the center of the pad having apertures, the discrete region not extending to any of the peripheral edges. Also, apertures and deformations could be in a stripe pattern with the stripes generally transversely aligned.

FIG. 2 shows a two-layer facing layer 1 having a topsheet 26 layer and a secondary topsheet 27 layer. It is recognized that the facing layer 1 need not be limited to any particular number of layers, and can have only one, or it can have three or more.

Without being bound by theory, it is believed that superior fluid acquisition is obtained by having the topsheet 26 layer and the secondary topsheet 27 layer intimately contacting one another by processing the two together as a composite web material by the method disclosed below. In this manner, the topsheet 26 and the secondary topsheet 27 become somewhat intermeshed and function as a single facing layer 1.

Figure 3:
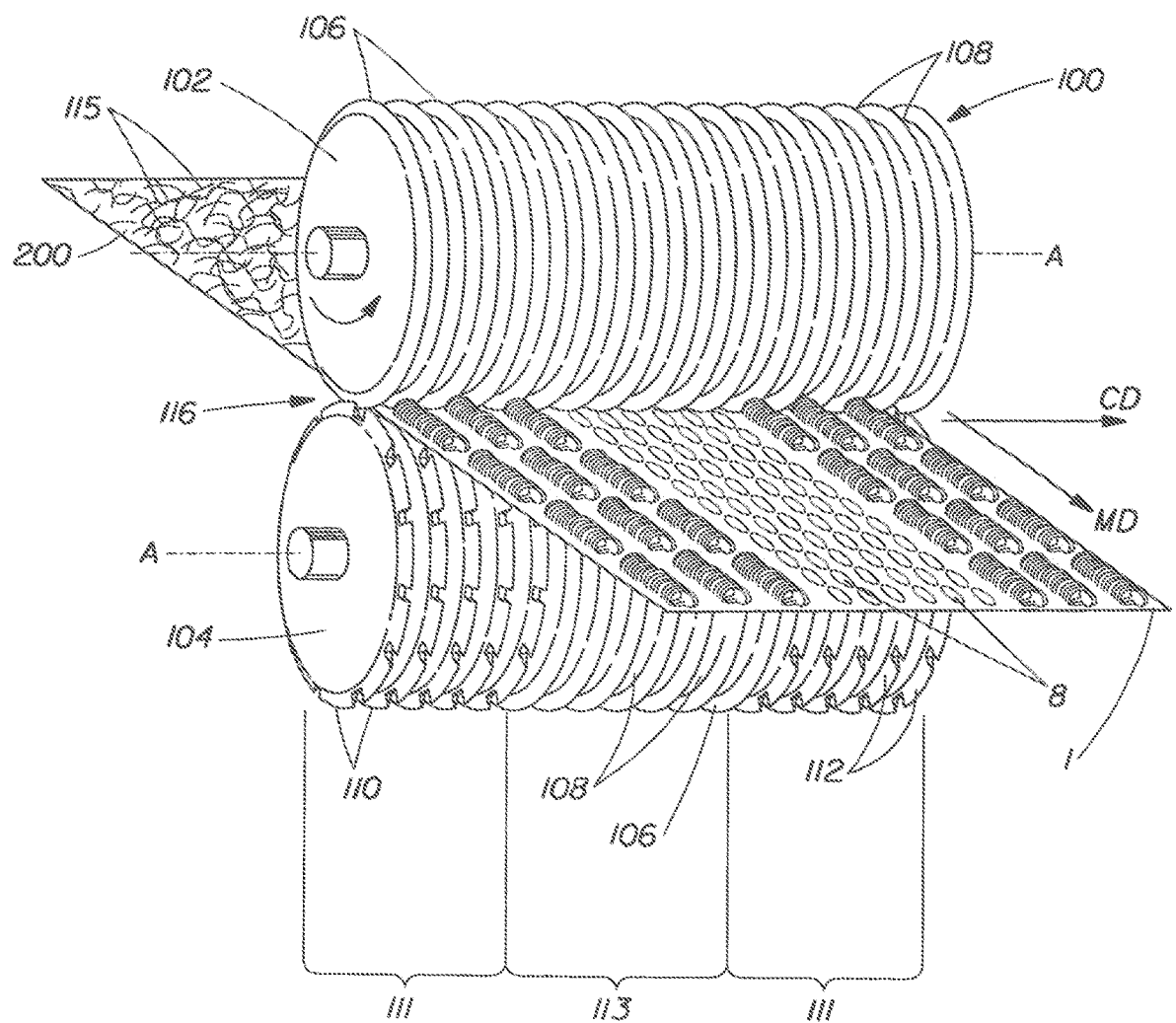
FIG. 3 is a perspective view of an apparatus for making the present invention.

FIG. 3 shows a method for making facing layer 1 of the present invention that is suitable for use on sanitary napkin 20. Facing layer 1 is formed from a generally planar, two dimensional nonwoven precursor web 200 on apparatus 100, the apparatus preferably being oriented for continuous web processing with respect to a machine direction (MD) and a cross machine direction (CD) as is commonly known in the art of nonwoven webs. Precursor web 200 has formed therein in predetermined regions a plurality of melt-weakened portions 115 prior to entering nip 116. Melt-weakened portions are formed in predetermined regions of web 200 by thermal point calendaring in the predetermined regions, the predetermined regions corresponding to first region(s) 2 of facing layer 1, that is, the region where apertures are ultimately desired. Each melt-weakened portion of the predetermined region is generally elongated and oriented in the MD. Upon stretching in the CD in the portion of the apparatus 100 corresponding to the region 113, the melt-weakened portions rupture to form apertures 8. In one embodiment, the melt-weakened portions 115 are limited to the central region of web 200, that is, the region corresponding to the central first region 2 of sanitary napkin 20 in FIG. 1.

The apparatus 100 comprises a pair of rolls 102 and 104, each rotating about parallel axes A, and is similar in many respects to the apparatuses described in the above-mentioned U.S. Pat. Nos. 5,916,661 and 5,628,097, and U.S. Pat. No. 5,518,801 issued to Chappell et al., each of which are hereby incorporated herein by reference. The primary difference is the combination in one apparatus the benefit of aperture-forming rolls as taught in U.S. Pat. Nos. 5,916,661 and 5,628,097, and rib-like element-forming rolls as taught in U.S. Pat. No. 5,518,801. By combining both into one apparatus to form both apertures and rib-like elements in one facing layer 1, the sanitary napkin of the present invention provides for significant benefits over prior art sanitary napkins. In particular, the sanitary napkin of the present invention is better at keeping the body of the wearer clean than previously-known sanitary napkins. It is believed that the apertures 8 of facing layer permit rapid acquisition of menses into the core 24, and the rib-like elements 10 serve to stop lateral fluid flow. As well, rib-like elements 10 serve as a plurality of "wipers" to constantly wipe the skin with the body movements of the wearer.

The apparatus 100 shown in FIG. 3 comprises a roll 102 comprising a plurality of circumferentially-extending ridges 106 separated by grooves 108, as disclosed in the above-mentioned patents and as well known in the art of "ring-rolling". A second, intermeshing roll 104 comprises a first region 113 having essentially matching roll 102 and having ridges 106 separated by grooves 108. The intermeshing ridges 106 and grooves 108 of rolls 102 and 104 incrementally stretch precursor web 200 to form apertures 8 as disclosed in U.S. Pat. Nos. 5,916,661 and 5,628,097. Of course, precursor web 200 has melt-weakened regions 115 formed therein prior to precursor web 200 entering the nip 116 of apparatus 100.

In addition to region 113, roll 104 has two regions 111 comprising ridges having formed therein teeth 110, the toothed ridges separated by grooves 112. Ridges 106 of roll 102 intermesh with the grooves 112 of roll 104 to form the rib-like elements 10 of second region(s) 3.

In this manner a web suitable for a facing layer 1 is produced, the facing layer 1 having both first regions 2 and second regions 3 comprising apertures 8 and rib-like elements 10, respectively, and suitable for use on a sanitary napkin, as shown in FIG. 1. Facing layer 1 has a first region 2 defined on both sides of facing layer 1 by having a plurality of spaced apart apertures 8. A second region 3 is defined by a plurality of spaced-apart rib-like elements 10 which are integral extensions of the fibers of the precursor web 200.

One advantage of the apparatus described above is that the facing layer can be produced in-line with other production equipment on a manufacturing line for producing disposable absorbent articles. For example, an apparatus such as the above-disclosed thermal point calendaring rolls for making melt-weakened portions 115 and the pair of rolls 102 and 104, can be made as a unit operation that can be inserted into an existing manufacturing line. As unit operations themselves, such apparatuses can be modular such that they can be changed out relatively quickly and easily with other modular unit operations. When used as part of a manufacturing line for sanitary napkins, for example, the constituent rollers need not be much wider than the product itself, thereby providing for relatively quick and easy installation and removal. Various patterns of first region 2 and second region 3 can therefore be implemented with a minimum of manufacturing line interruption.

In one embodiment, the facing layer 1 of the present invention can have a lotion applied thereto to provide even more and better benefits. In one embodiment a lotion as disclosed in co-pending U.S. application Ser. No. 10/262,036, filed Oct. 1, 2002, which is hereby incorporated herein by reference.

Apertures 8, and discrete raised, out-of-plane deformations 10 serve to add significant extensibility to facing layer 1. For example, it has been found that sanitary napkins of the present invention having significant caliper (thickness) due, for example, to a relatively thick absorbent core, can have deep-embossed channels produced therein, the channels having a tendency to stay deep-embossed.

Figure 4:
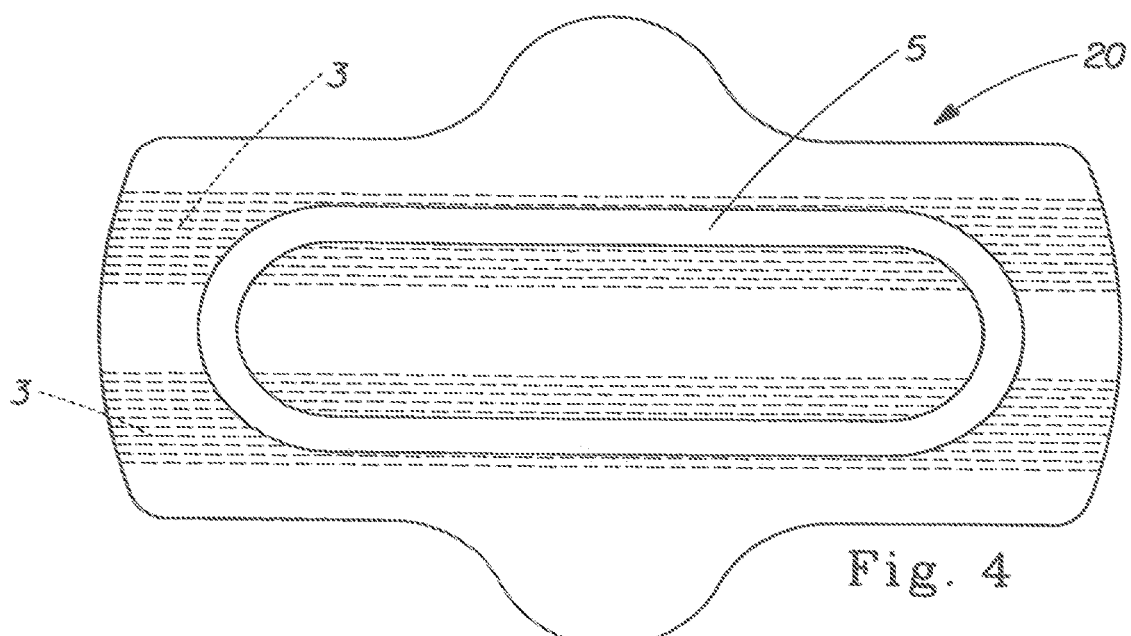
FIG. 4 is a plan view of a sanitary napkin of the present invention having deep-embossed channels.
Figure 5:
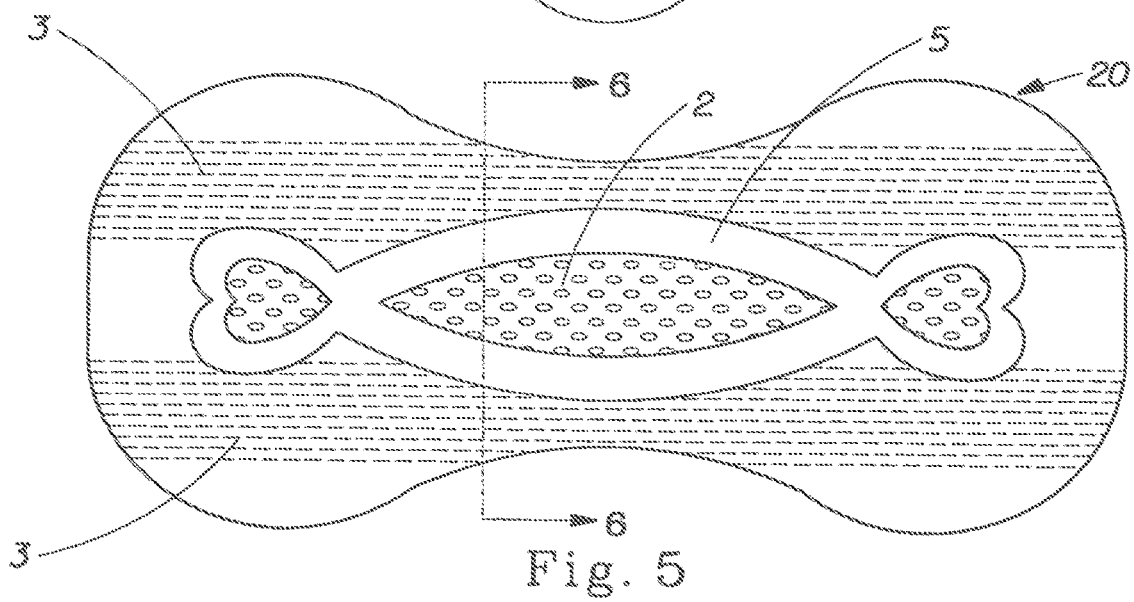
FIG. 5 is a plan view of a sanitary napkin of the present invention having deep-embossed channels.
Figure 6:
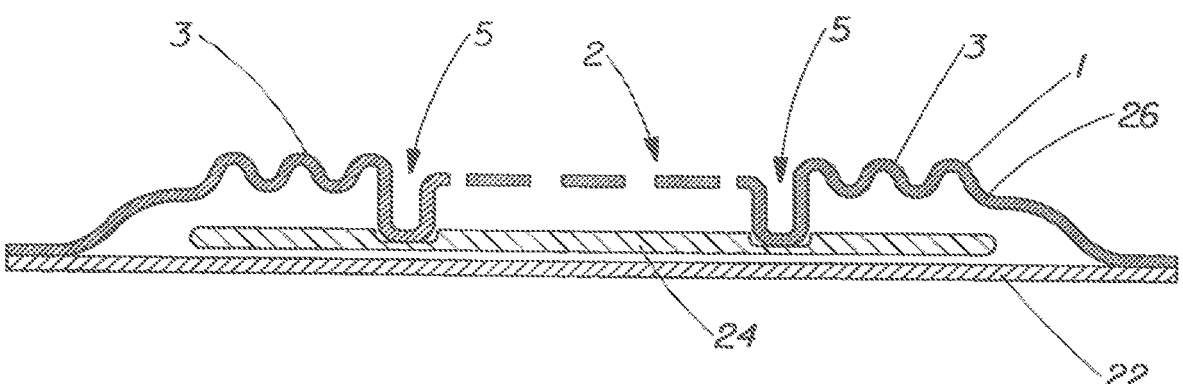
FIG. 6 is cross sectional view of Section 6-6 of FIG. 5.

As shown in FIGS. 4-6, a channel 5 can be deep-embossed into sanitary napkin 20. Embossing facing layer 1 deep into absorbent core 24 provides for a fluid-impeding channel that helps contain fluid flow, and, as well, adds to the aesthetic appearance of the sanitary napkin 20. In prior art sanitary napkins, deep-embossing is often not effective due to the lack of channel retention during packaging, storage, or use. It is believed that the elastic tension of a normal topsheet works to slowly pull the embossing out after it is put in. The inherent extensibility of the facing layer 1 of the present invention, however, permits significant extension of the facing layer 1 into the deep-embossed channel 5, with little or no restoring force present.

Also as shown in FIGS. 4 and 5, the deep-embossed channel 5 can define at least one interior portion which is the portion of the sanitary napkin circumscribed by the channel 5. In the embodiment shown in FIG. 5, for example, three interior portions are defined by channel 5. In a preferred embodiment, the first region is disposed substantially within the interior portion(s) defined by channel 5.

As shown in cross section in FIG. 6, the deep embossed channels can significantly compress the absorbent core 24 in the region of channel(s) 5. This provides for additional fluid containment near the central portion of sanitary napkin 20.

By way of example, deep embossed channels 5 can have a depth dimension in the Z-direction of at least about 50% of the caliper (thickness in the Z-direction) of the sanitary napkin 20, more preferably about 60%, 70%, 80% or 90% of the caliper. Thus, if the caliper of the sanitary napkin 20 is 10 mm, the depth of embossment of channel(s) 5 can be 6 mm, 7 mm, 8 mm, or 9 mm. Caliper and depth dimensions can be average dimensions if either are not consistent across the entire sanitary napkin.

As shown in FIG. 4, in one embodiment facing sheet 1 does not comprise apertures. In this embodiment, the raised, out-of-plane deformations 10 provide sufficient extensibility to facing sheet 1 to permit the formation and retention of deep-embossed channels 5.

By "retention" of deep-embossed channels 5 is meant that after being packaged and/or used, the channels 5 retain at least 50% of their original depth dimension, more preferably 60%, 70%, 80%, 90% or 100%. Depth can be measured by any techniques known in the art, including by simple digital depth gauge, using an average depth if depth is variable over the length of channels 5.

Nonwoven precursor webs 200 can be any known nonwoven webs or composites of two or more nonwoven webs, each comprising fibers having sufficient mechanical (e.g., elongation) properties to be formed into web 1 as described more fully below. Fibers can be monocomponent, bicomponent, biconstituent, or capillary channel fibers.

As used herein, the term "nonwoven web" refers to a web having a structure of individual fibers or threads which are interlaid, but not in an identifiable manner as in a woven or knitted fabric. Nonwoven webs or fabrics have been formed from many processes, such as, for example, meltblowing processes, spunbonding processes, and bonded carded web processes. The basis weight of nonwoven fabrics is usually expressed in grams per square meter (gsm) and the fiber diameters are usually expressed in microns. Fiber size can also be expressed in denier. The basis weight of precursor web 200 (which can be a single layer or a composite of more than one layer) can range from 10 gsm to 200 gsm, depending on the ultimate use of the web 1.

The constituent fibers of nonwoven precursor web 200 can be polymer fibers, and can be monocomponent, bicomponent, and/or biconstituent, capillary channel fibers, and can have major cross-sectional dimensions (e.g., diameter for round fibers) ranging from 5-200 microns. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "capillary channel fibers" refers to fibers having capillary channels. Such fibers can be hollow fibers, for example, but are preferably fibers having capillary channels on their outer surfaces. The capillary channels can be of various cross-sectional shapes such as "U-shaped", "H-shaped", "C-shaped" and "V-shaped".

While various preferred embodiments of the invention have been disclosed herein, such embodiments are not intended to limit the scope of the invention. As can be understood from the above description of sanitary napkin 20 of the present invention, many various structures can be made without departing from the scope of the present invention as claimed in the appended claims.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A disposable absorbent article having a longitudinal axis defining a longitudinal orientation and longitudinally-oriented side edges, a transverse axis orthogonal to the longitudinal axis, and a thickness measured orthogonal to a plane defined by the longitudinal axis and the transverse axis, the disposable absorbent article comprising:
    a facing layer, a backsheet, and an absorbent core disposed between the facing layer and the backsheet, wherein the facing layer comprises a composite material comprising a plurality of apertures extending through the facing layer, wherein the composite material comprises a first nonwoven layer and a second nonwoven layer, wherein the second nonwoven layer comprises a plurality of fibers having a diameter of greater than 7 microns, and wherein the first layer forms a portion of a body-facing surface of the disposable absorbent article.

2. The disposable absorbent article of claim 1, wherein the facing layer further comprises a plurality of out-of-plane deformations.

3. The disposable absorbent article of claim 2, wherein the plurality of out-of-plane deformations are discrete and comprise a distal end and sidewalls.

4. The disposable absorbent article of claim 3, wherein said out-of-plane deformations are soft, resilient, textured wipers.

5. The disposable absorbent article of claim 3, wherein said out-of-plane deformations are soft, resilient, rib-like elements.

6. The disposable absorbent article of claim 3, wherein the distal end is arched.

7. The disposable absorbent article of claim 3, wherein a plurality of depressions are disposed between adjacent out-of-plane deformations.

8. The disposable absorbent article of claim 1, wherein the facing layer composite material comprises a nonwoven web.

9. The disposable absorbent article of claim 1, wherein said facing layer composite material comprises a spunbonded nonwoven web.

10. The disposable absorbent article of claim 1, wherein the facing layer composite material comprises a bonded carded nonwoven web.

11. The disposable absorbent article of claim 1, wherein the facing layer composite material comprises a topsheet and a secondary topsheet, wherein the topsheet and the secondary topsheet are in intimate contact with one another via mechanical manipulation of the composite web.

12. The disposable absorbent article of claim 1, wherein the out-of-plane deformations are arranged in a first pattern.

13. The disposable absorbent article of claim 12, wherein the apertures are arranged in a second pattern.

14. The disposable absorbent article of claim 13, wherein the first pattern and the second pattern do not overlap one another.

15. The disposable absorbent article of claim 1, wherein the composite material comprises at least two nonwoven webs.

* * * * *